United States Patent
Koenig et al.

(10) Patent No.: US 9,176,309 B2
(45) Date of Patent: Nov. 3, 2015

(54) FLEXIBLE NONLINEAR LASER SCANNING MICROSCOPE FOR NONINVASIVE THREE-DIMENSIONAL DETECTION

(71) Applicant: JenLab GmbH, Jena (DE)

(72) Inventors: Karsten Koenig, Saarbruecken (DE); Martin Weinigel, Jena (DE)

(73) Assignee: JenLab GmbH, Jena (DE)

( * ) Notice: Subject to any disclaimer, the term of this patent is extended or adjusted under 35 U.S.C. 154(b) by 231 days.

(21) Appl. No.: 13/645,607

(22) Filed: Oct. 5, 2012

(65) Prior Publication Data

US 2013/0088709 A1   Apr. 11, 2013

(30) Foreign Application Priority Data

Oct. 8, 2011 (DE) .......................... 10 2011 115 944

(51) Int. Cl.

| | |
|---|---|
| *G01N 21/00* | (2006.01) |
| *G01J 3/52* | (2006.01) |
| *G01B 11/30* | (2006.01) |
| *G02B 21/00* | (2006.01) |
| *A61B 5/00* | (2006.01) |

(52) U.S. Cl.
CPC .......... *G02B 21/0032* (2013.01); *A61B 5/0068* (2013.01); *G02B 21/0028* (2013.01); *G02B 21/0076* (2013.01); *A61B 5/6835* (2013.01); *A61B 2560/0437* (2013.01)

(58) Field of Classification Search
CPC .. A61B 5/0059; A61B 5/0066; A61B 5/0095; A61B 8/0858; G02B 1/0028; G02B 1/0032; G02B 1/0076
USPC ........................................... 356/72, 600, 422
See application file for complete search history.

(56) References Cited

U.S. PATENT DOCUMENTS

| | | | |
|---|---|---|---|
| 4,659,916 A | 4/1987 | Müller et al. | |
| 5,034,613 A | 7/1991 | Denk et al. | |
| 5,463,215 A | 10/1995 | Alfille | |
| 7,148,683 B2 * | 12/2006 | Xiang et al. | 324/300 |
| 7,817,268 B2 * | 10/2010 | Bakker et al. | 356/317 |
| 2008/0081950 A1 | 4/2008 | Koenig et al. | |
| 2010/0294949 A1 * | 11/2010 | Sasaki et al. | 250/458.1 |
| 2012/0080616 A1 | 4/2012 | Schoenborn | |

FOREIGN PATENT DOCUMENTS

| | | | |
|---|---|---|---|
| DE | 20117294 U1 | 2/2003 | |
| DE | 20306122 U1 | 10/2003 | |
| DE | 202010009249 | * 9/2010 | A61B 5/00 |
| DE | 202010009249 U1 | 9/2010 | |
| DE | 102009029831 A1 | 1/2011 | |
| DE | 102010047578 A1 | 4/2012 | |
| EP | 1929939 A2 | 6/2008 | |
| WO | 2012062306 A2 | 5/2012 | |

* cited by examiner

*Primary Examiner* — Tarifur Chowdhury
*Assistant Examiner* — Sunghee Y Gray
(74) *Attorney, Agent, or Firm* — Patentbar International, P.C.

(57) ABSTRACT

A nonlinear laser scanning microscope for flexible, noninvasive three-dimensional detection comprising a measuring head which is flexibly connected to at least one radiation source by transmission optics and can be freely positioned in space, at least one controllable tilt mirror is arranged for aligning the excitation beam in order to keep the excitation beam concentric to an aperture-limited optical element of the measuring head, a test beam which is coupled out of the excitation beam onto a spatially resolving photodetector for monitoring the center alignment of the test beam as a conjugate position to the target position of the excitation beam and directional stabilizing the excitation beam by a control unit of the tilt mirror depending on a determined deviation.

16 Claims, 6 Drawing Sheets

FLEXIBLE NONLINEAR LASER SCANNING MICROSCOPE FOR NONINVASIVE THREE-DIMENSIONAL DETECTION

FIELD OF THE INVENTION

The invention is directed to a nonlinear laser scanning microscope for flexible, noninvasive three-dimensional detection, particularly in living matter (in vivo), preferably in the skin of animals, in plants and cell cultures, and in nonliving matter such as, for example, minerals, textiles and works of art. By nonlinear laser scanning microscope or microscope with multiphoton (MP) excitation is always meant hereinafter a microscope having two-photon or multiphoton excitation.

BACKGROUND OF THE INVENTION

Two-photon microscopes and multiphoton tomographs (MPT) in which fluorescence signals and SHG (Second Harmonic Generation) signals are excited in biological molecules in vivo by pulsed laser radiation in the near infrared region and are detected by suitable highly sensitive, fast receivers are known (e.g., U.S. Pat. No. 5,034,613 A, DE 201 17 294 U1; DE 203 06 122 U1). Further, nonfluorescing and non-SHG active components such as water and lipids can be displayed by means of CARS (Coherent Anti-Stokes Raman Scattering) microscopes and CARS tomographs (see, e.g., DE 10 2010 047 578 A1, not previously published).

Horizontal resolutions in the submicrometer range and scan areas (object regions) of several hundred micrometers in three dimensions are achieved by these nonlinear optical microscopes and tomographs.

Nonlinear microscopes and tomographs of this kind are based on the use of rigid designs and vibration-damped optical stage arrangements. They can be operated as either upright or inverted optical microscope arrangements. However, no high-resolution imaging systems (with a lateral resolution of about 1 μm or less) permitting a free positioning of the measuring head at the required lateral and axial resolution in the submicrometer range are known for nonlinear microscopy or tomography.

A beam transmission required for this purpose can be realized by optical fiber systems or as a free-beam transmission system. The accuracy of free-beam laser transmission systems such as are known, for example, in the form of articulated mirror arms is affected by mechanical deviations, mechanical stresses and temperature drift within the mechanical cage structure of these arms. In various configurations of the articulated arm, the effect on the mechanical axis of the articulated mirror arm (due to temperature drift, for example) leads to a deviation of the position of the laser beam at the output of the articulated arm relative to the target position or mechanical axis so that a reliable scanning of a measurement object by means of high-resolution focusing optics at different orientations of the measuring head is possible only to a limited extent. The fluctuations in the position of the laser beam at the output of the optical articulated arm can be subsumed under the concept of "accuracy of the transmission system."

The accuracy of the laser beam transmission is further influenced by the given length of the optical beam path of an articulated arm and the beam position stability (pointing ability) of the laser.

In the present instance, pointing ability refers to the change in the directional stability of the laser radiation at the direct output of the laser resulting from the thermally induced effect on the resonator configuration of the laser.

The coupling of the laser radiation into an articulated mirror arm is especially critical. In-coupling is optimal when the optical axis of the laser beam coincides with the mechanical (entrance) axis of the articulated arm (collinearity). Deviations occurring in this respect influence accuracy apart from the above-mentioned mechanically caused and thermally caused deviations of the articulated arm.

While the deviations to be compensated in guiding the laser beam are reduced exclusively to the in-coupling and out-coupling of the beam when using fiber transmission optics, the basic problem of undesirable laser beam deviation at the target site remains. In particular, there is also the risk of unwanted coupling into the fiber sheath (cladding).

U.S. Pat. No. 5,463,215 A discloses a device for aligning a light beam for coupling thereof into an optical fiber in which a portion of the laser beam that is not coupled into the fiber diameter is coupled out to a detector device via two annular conical mirrors which are arranged as retroreflectors and a mirror rotating on a ring at 45°. By synchronizing the detector with the position of the revolving mirror, a deviation from the collinearity of the laser axis and fiber axis and a defocusing can be detected. Further, an overlapping illumination of the fiber input (i.e., beam diameter greater than fiber diameter) is required and, therefore, a loss of intensity is already inevitable from the outset.

Accordingly, the prior art presents the following disadvantages:

owing to their rigid construction, conventional two-photon microscopes and multiphoton tomographs (MPTs) present a limited range of application and are, for example, unsuitable for multifunctional examinations on the human body;

for realizing a flexible construction, the mechanical tolerances of beam-guiding systems are too large to ensure a sufficiently constant illumination of a measurement spot for a reproducible irradiation of the scan site permitting a submicrometer resolution; and in multiphoton microscopy, the limitation of imaging to the detection of autofluorescence of endogenous substances and to nonlinear frequency multiplication of certain molecules is often disadvantageous, and the desirable combination with CARS systems could only be realized heretofore in rigid systems because of the strict requirements respecting collinearity.

SUMMARY OF THE INVENTION

Therefore, it is the object of the invention to provide a mobile, flexibly usable nonlinear laser scanning microscope for noninvasive three-dimensional detection for multivalent high-resolution nonlinear examinations, particularly of skin, tissue in the urogenital area, in the oral cavity and in the eye area of the human body, but also in plants, animals, cell cultures and in nonliving material, which permits a reproducible illumination of the focusing optics with unlimited flexibility of the measuring head. An extended object is to realize a reproducibly convergent, simultaneous application of two beam paths for purposes of combining different measuring methods, preferably MP tomography and CARS tomography, in a shared flexible measuring head.

According to the invention, in a flexible nonlinear laser scanning microscope for noninvasive three-dimensional detection containing at least one radiation source which generates an excitation beam for initiating a secondary radiation emitted by atoms and molecules, flexible transmission optics for transmitting the radiation to a measuring head having focusing optics by which the radiation is focused in a measurement object and the emitted secondary radiation is guided back and directed to at least one detector system, the above-stated object is met in that the measuring head is connected to the at least one radiation source so as to be freely pivotable and rotatable in space and flexibly positionable so that upright microscopy, inverted microscopy and microscopy at any solid angles can be carried out, in that at least one controllable tilt mirror is arranged for deflection and orientation of at least one excitation beam of pulsed laser radiation of the at least one radiation source in order to align the at least one excitation beam in the measuring head through the transmission optics in such a way that the excitation beam is arranged concentric to an aperture-limited optical element of the measuring head in any position of the measuring head, in that a beamsplitter for coupling a test beam out of the excitation beam is arranged in the measuring head in front of the focusing optics, a spatially resolving photodetector for determining the beam position of the excitation beam, which beam position is defined in a target position, is arranged in a position of the test beam conjugate to the target position, wherein a center alignment of the test beam on the photodetector corresponds to the normal orientation of the excitation beam in the target position, and in that a control unit is provided for driving the controllable tilt mirror depending on a determined deviation of the test beam from its center alignment on the photodetector so as to achieve a stabilization of direction of the laser beam irrespective of the magnitude of the position-dependent impairment of the transmission optics.

The controllable tilt mirror is advantageously driven by means of a mirror holder based on a drive principle from the group comprising capacitive, inductive or piezo actuators, stepping motors or DC motors.

The controllable tilt mirror can advisably be realized by means of a two-axis mirror holder or by means of two single-axis mirror holders.

The entrance pupil of the focusing optics or of another aperture-limited optical element is advantageously selected as target position for the stabilized alignment of the at least one excitation beam.

It has proven advisable that the beamsplitter for generating the test beam is constructed either as a reflection beamsplitter or as a transmission beamsplitter depending on the guiding of the at least one excitation beam in the measuring head.

The beamsplitter for coupling out the test beam can advantageously be constructed simultaneously as a dichroic mirror for collinear in-coupling of two different excitation beams.

The position-sensitive photodetector for detecting the test beam as equivalent of the excitation beam in the target position is preferably a circular photodiode. However, alternatively, rectangular detector shapes or other detector shapes as well as spatially resolving (segmented) receivers such as quadrant photodiodes, orthogonally arranged lateral effect diodes, crossed detector arrays (CCD or CMOS), CCD matrix arrays or CMOS matrix arrays can also be used.

In addition to controlling the beam stability in the transmission optics, the position-sensitive photodetector can also advantageously determine and correct the pointing stability of the laser.

The detector system for the secondary radiation emitted from the measurement object is preferably constructed with a detector for MPT imaging or SHG imaging so as to provide a flexible diagnostic system for fluorescing substances which permits free positioning of the measuring head in space by means of a flexible optical articulated arm of low mechanical accuracy and ensures a reproducible MPT imaging.

The detector system for the secondary radiation can be formed in a particularly advantageous manner with a plurality of detectors for MPT imaging, SHG imaging and CARS imaging so as to provide a flexible diagnostic system for fluorescing and nonfluorescing substances in living matter which by means of a shared flexible optical articulated arm permits any free positioning of the shared measuring head in space and generates a simultaneous, co-located imaging from MPT signals, SHG signals and CARS signals. In so doing, the diagnostic system which is combined in this way for fluorescing and nonfluorescing substances can also conveniently permit the free positioning of the shared measuring head via a flexible optical articulated arm and a separate optical fiber. Further, it is possible to realize a free positioning of the shared measuring head for simultaneous, co-located imaging in the flexible combined diagnostic system by means of two separate optical fibers.

Further, in a compact variant the detector system for the secondary radiation can have a shared measuring detector for MPT imaging and for CARS imaging, wherein means are provided for periodically interrupting the CARS excitation which allow a separation of MPT imaging with respect to a combined signal display.

The detector system advantageously has TCSPC detectors for MPT imaging for time-correlated single-photon counting. In so doing, the detector system is conveniently outfitted with an additional trigger diode which makes use of a back reflection of a beamsplitter provided in the measuring head for coupling out the measurement signal.

In an advantageous embodiment of the flexible laser scanning microscope, the measuring head is mechanically supported by means of a flexible supporting arm which can be locked in any position at a mobile base device which positively drives the transmission optics, wherein at least one radiation source for generating pulsed excitation radiation, an optics unit for the synchronization of the pulsed excitation radiation and alignment on at least one transmission optics to the measuring head and the control unit for stabilizing the direction of the excitation radiation in the measuring head, and an evaluating unit for processing the signals which are transmitted from the detector system of the measuring head for imaging display by a display unit are provided in the base device.

The invention is based on the consideration that there are generally two possibilities for achieving accuracy of a flexible beam transmission in articulated mirror arms, namely, through the use of largely bulky, heavy and cost-intensive opto-mechanical cage systems or through the use of a sophisticated directional stabilization of the laser radiation.

The invention meets these divergent requirements with a technologically simple, cost-effective and compact directional stabilization for laser radiation (or incoherent radiation) having for purposes of minimizing deviations a detector, a control unit and an actuator. Depending on the detected deviation in a conjugate target plane within an unrestrictedly flexible measuring head, a correction of the beam direction of the laser beam is carried out by means of the control unit (simple logic circuit) before this laser beam is coupled into the illumination and recording system (focusing optics) of the measuring head. At the same time, this beam stabilization also ensures the collinearity of the measurement radiation when a plurality of excitation beams are used.

Accordingly, the requirements imposed on a mechanical cage structure of an articulated mirror arm with regard to the required accuracy of the beam guidance are reduced and the resulting savings on volume and weight comply with the flexibility and mobility of the microscope measuring system (e.g., a tomograph). Advantages of the directional stabilization, e.g., compact, small-sized construction and cost effectiveness, are evidenced particularly in the fiber coupling input in fiber transmission systems.

The solution according to the invention is further characterized in that an object site to be examined by a microscope imaging system with flexible measuring head can be examined simultaneously by different measurement methods, e.g., by means of high-resolution multiphoton fluorescence microscopy, multiphoton SHG microscopy and/or CARS microscopy. In so doing the different excitation beams of one or more short-pulse lasers can be transmitted via one and the same flexible optical articulated arm or a flexible optical articulated arm and an additional optical fiber or via two optical fibers and can be controlled and adjusted by the same device for beam stabilization.

With the invention it is possible to realize a compact, flexible nonlinear laser scanning microscope for noninvasive three-dimensional detection for imaging examinations with submicrometer resolution which permits a reproducible illumination of the measurement object with unlimited flexibility of the measuring head. Further, beam paths of different measurement methods, preferably of multiphoton fluorescence microscopy, multiphoton SHG microscopy and/or CARS microscopy can be combined in a shared flexible measuring head and in so doing the same reproducible illumination and pinpointed (cell-by-cell) scanning can be realized.

BRIEF DESCRIPTION OF THE DRAWINGS

The invention will be described more fully in the following with reference to embodiment examples. The drawings show.

DETAILED DESCRIPTION OF THE PREFERRED EMBODIMENTS

Figure 1:
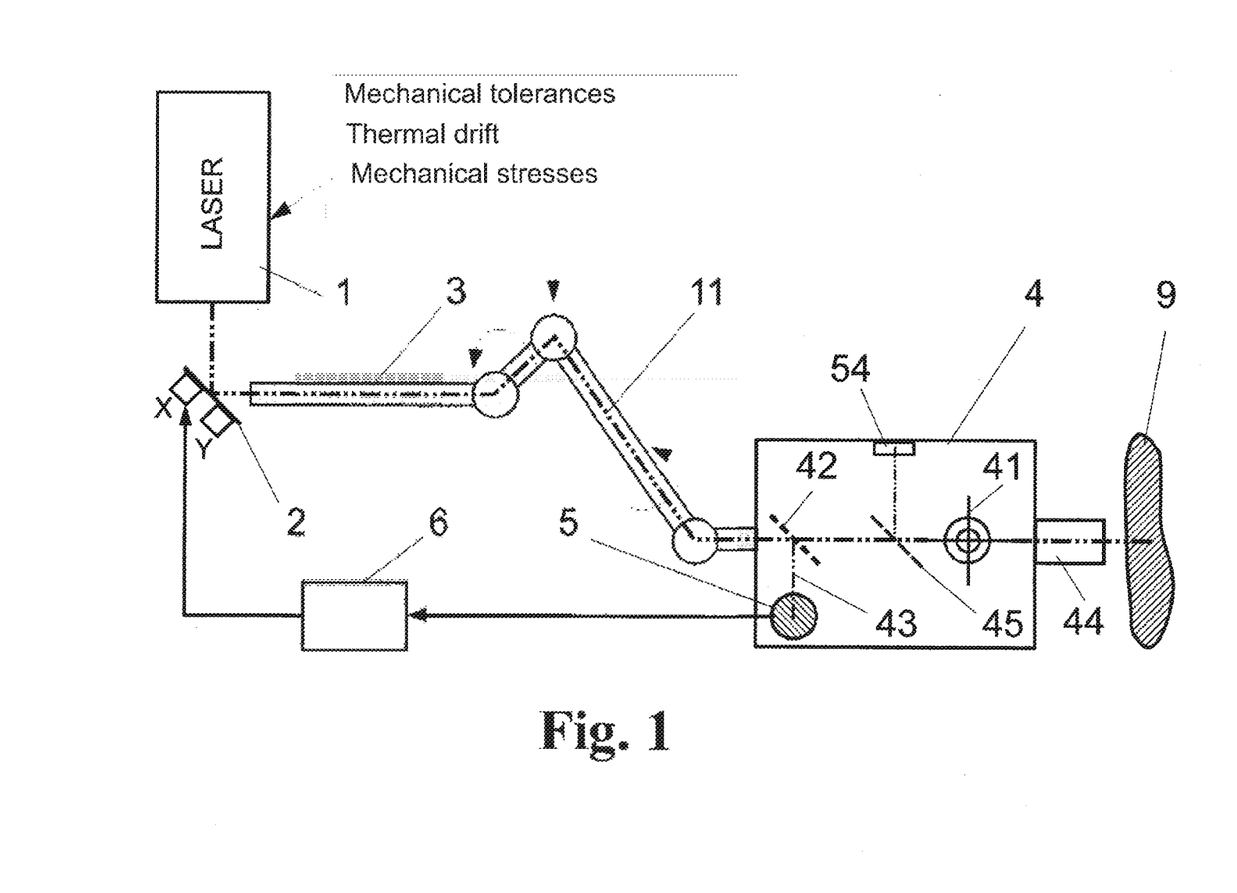
FIG. 1 a schematic diagram of the invention for aligning a laser beam on a target point in a measuring head using an articulated mirror arm as beam-guiding system.

FIG. 1 shows the basic construction of the system. A laser 1, preferably a single-mode (transverse mode) laser, with a circular beam profile (or other beam profile such as, e.g., elliptical or multimode laser beams) transmits a laser beam 11 to an adjustable tilt mirror 2 by which the laser beam 11 is coupled into transmission optics 3 and is guided to a target position 41 within a measuring head 4. A small proportion (<10%, for example) of the laser beam 11 is coupled out as test beam 43 to a spatially resolving photodetector 5 by means of a beamsplitter 42 arranged in the measuring head 4. The position of the spatially resolving photodetector 5 is arranged conjugate to a target position 41 so that the photodetector 5 is sensitive to positional deviations of the beam profile 13 (shown only in FIG. 2) of the laser beam 11 (or of the test beam 43 coupled out therefrom) from a normal or center position. This means that the test beam 43 has an optical axis deviating with respect to the laser beam 11 (for example, by the angle of 90°).

Figure 2:
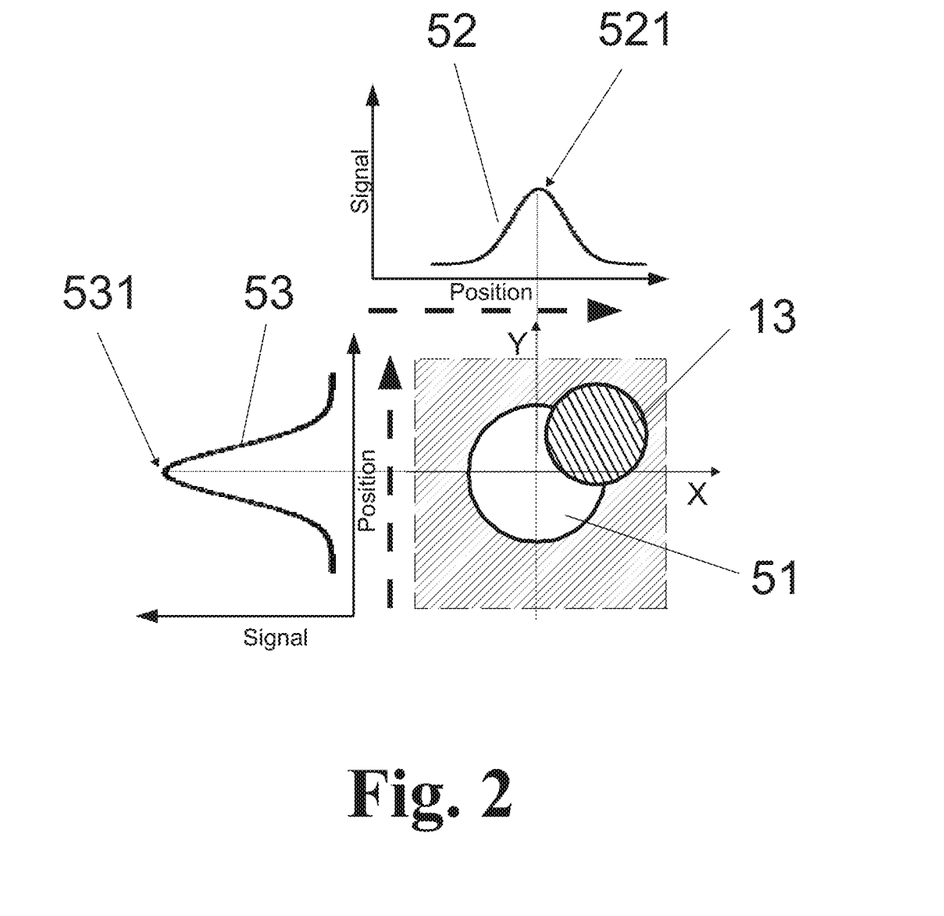
FIG. 2 an illustration of the detection principle for the beam deviation in a conjugate target plane using a circular photodiode.

A control unit 6 (which can be realized as a simple logic unit) evaluates the output signal of the photodetector 5 and adjusts the angular orientation of the adjustable tilt mirror 2 to a maximum of the photodetector signal depending on the deviation of the test beam 43 (center or power centroid of the beam profile 13 as is shown in FIG. 2) from the center position of the photodetector 5.

FIG. 2 shows the spatially resolving photodetector 5 as an individual large-area circular photodiode 51 inside a shaded square. However, there are many other possibilities for the detection of positional deviations of the beam profile 13 of the laser beam 11. They can be realized by detectors measuring in a spatially resolving manner such as quadrant photodiodes, by two orthogonally arranged lateral effect diodes (position sensitive device (PSD)), crossed detector rows (charged-coupled device (CCD) or complementary metal oxide semiconductor (CMOS)), a CCD matrix or CMOS matrix; the two-dimensional sensor arrays are constructed with circularly connected (binning) area elements or record in an integrating manner in combination with a light-conducting fiber. Further, less common detector systems having a moving gap (scanning slit detector) can be used.

When there is a change in the angular position of the adjustable tilt mirror 2 (referring to FIG. 1), the beam profile 13 (which is assumed to be circular in the present case) of the laser beam 11 is deflected inside the shaded square. In case of a partial overlapping of the areas of the beam profile 13 and photodetector 5, which should advantageously be constructed as a circular photodiode 51 corresponding to the circular beam profile 13, an output signal is generated based on the photocurrent of the photodetector 5 generated by the incident laser radiation.

The aim of the arrangement according to FIG. 1 is to permanently center the beam profile 13 in the center of the photodetector 5. The position of the beam profile 13 is defined here by the coordinates X and Y within a Cartesian coordinate system associated with the ideal position of the laser beam 11 in the target position 41 of the measuring head 4. The same coordinate system is associated with the conjugate position in which the photodetector 5 is arranged and forms the basis for the detection of the beam deviation. The origin of the Cartesian coordinate system of the target position 41 in FIG. 1 correlates with the center of the circular photodiode 51, since the latter is arranged in a plane conjugate to the target position 41.

The output signal of the photodetector 5 is produced by a position-dependent superposition or convolution of the sensitivity distribution of the circular photodiode 51 with the intensity function of the beam profile 13 as is illustrated by way of example in FIG. 2 as approximate Gaussian distribution for the signal component 52 in the X coordinate and as qualitatively identical signal component 53 in the Y coordinate inside the shaded square (assumed coordinate system).

As a result of dividing the output signal into X component and Y component, the position of the beam profile 13 can be varied by means of the angular deflection of the adjustable tilt mirror 2 and can be adjusted by steps (e.g., first for the X coordinate and then for the Y coordinate to the maximum of the photodiode signal).

A deflection of the beam profile 13 in the X direction of a Cartesian coordinate system generates a position-dependent signal component 52 with a global maximum 521. The amplitude of the signal component 52 depends on the overlapping of the (circular) beam profile 13 and circular photodiode 51 or, more precisely, on the convolution of the intensity function of the laser beam 11 with the sensitivity function of the photodiode 51. The deflection angle of the laser beam 11 associated with the maximum 521 represents the sought-for coordinate in the X direction. With this, the sought-for correction position of the X axis of the tilt mirror 2 is determined and aligned. Starting from this X coordinate, a deflection in orthogonal direction (of the Y axis of the coordinate system) leads to a second signal component 53 of the circular photodiode 51 whose maximum 531 correlates with the sought-for coordinate in the Y direction. The sought-for correction position of the Y axis of the tilt mirror 2 is determined in this way and the tilt mirror 2 can be aligned in a corresponding manner. The amplitude of the signal component 53 is enlarged or maximized as a result of the first tracking movement by the enlarged overlap of the beam profile 13 and surface of the photodiode 51 relative to signal component 52.

Determining the coordinates once is sufficient for an ideal circular Gaussian beam profile 13 and an ideally circular photodiode 51. Here the origin of the Cartesian coordinate system of the target position 41 correlates with the center or centroid of the beam profile 13 after moving toward the coordinates in X direction and Y direction.

For a beam profile 13 which is not ideal (deviates from the circular Gaussian shape) or a noncircular photodetector 51, the coordinate search process in X direction and Y direction must be repeated a number of times. The result of the first alignment can then be tested again in the test beam 43 and, if necessary, the tilt mirror 2 can be readjusted again.

Accordingly, aside from circular (single-mode) beam profiles, multimode or asymmetrical beam profiles 13 can also be centered on the target position (iterative approximation) through repeated application of the centering process. In this case, rather than the center of an ideal circular beam profile 13, the intensity centroid of the beam profile 13 is aligned.

With the help of the information from the two signal components 52 and 53 of the circular photodiode 51 in coordinates X and Y, the adjustable tilt mirror 2 is aligned by the control unit 6 in such a way that the signal of the photodiode 51 is larger and the beam profile 13 (or its intensity centroid) is accordingly shifted to the center of the target plane 41.

For maximum accuracy in this control scheme, the signal components 55 and 56 must have a maximum 521 and 531, respectively, which is free of plateaus. This can be accomplished by matching the diameter of the circular photodiode 51 to the diameter of the beam profile 13, for which purpose the diameter of the photodiode 51 should be twice as large as the beam radius at 1/e2 of the intensity of the laser beam 1. Another possibility for determining the maximum 521 and 531, respectively, of signal components 52 and 53 as accurately as possible consists in a subsequent signal processing (e.g., Gaussian adaptation or low-pass filtration). This allows operation of the system also with long-coherence laser radiation sources in which the signal has interferences through multiple reflections at beamsplitters.

The dynamic range of the signal components 52 and 53 can be increased by using logarithmic amplifiers (not shown), which also guarantees the function of directional stabilization with lasers with variable output power.

Figure 4:
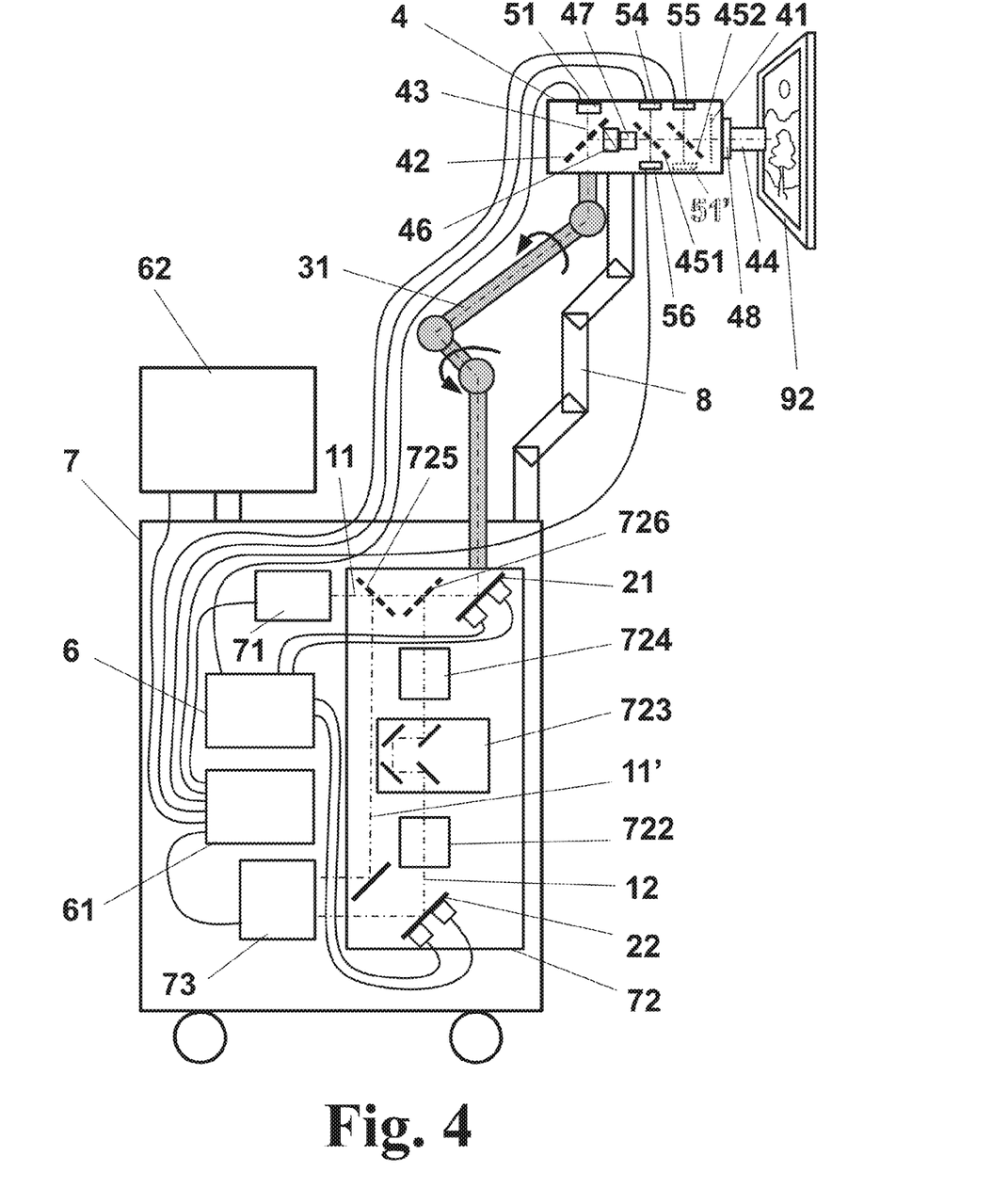
FIG. 4 a schematic diagram of an embodiment of the invention in a flexible laser scanning microscope with two detector systems using a shared articulated mirror arm as system for beam-guiding to the measuring head which is aligned for examination of a vertical measurement object (90-degree position), e.g., nonliving substances in a painting.

Depending on the direction in which the laser beam 11 is to be further guided in the measuring head 4, either the reflection (as is shown in FIG. 1) or the transmission of the laser beam 11 at the beamsplitter 42 (as is shown in FIG. 4) can be used for generating the test beam 43.

When using fiber transmission optics (as are provided in FIG. 5), the in-coupling of the laser beam 11 and accordingly the transmission of the system is influenced by thermal drift and mechanical stresses within the optics unit 72. When using monomode fibers having very small core diameters, the transmission can fall off by more than 10 percent within only a few minutes. This can result not only in deficient laser output in the measuring head 4 but also in destruction of the fiber transmission system through thermal interactions inside the fiber, which must be prevented at all costs.

The operating principle for the correction of the laser beam 11 and centering thereof in the core of fiber transmission optics is carried out analogous to the illustration in FIG. 1, wherein the function of the circular photodiode 51 described with reference to FIG. 2 can be represented by the circular core diameter of the transmission optics 3 formed as a fiber and by a photodetector 5 which is connected downstream of the latter and which integrates all of the transmitted light. In so doing the light-conducting fiber 32 together with a photodetector 5 in any form which is positioned behind the latter equivalently simulates a function, described with reference to FIG. 1 and FIG. 2, for the control of the circular photodiode 51.

Embodiment Example 1

Figure 3:
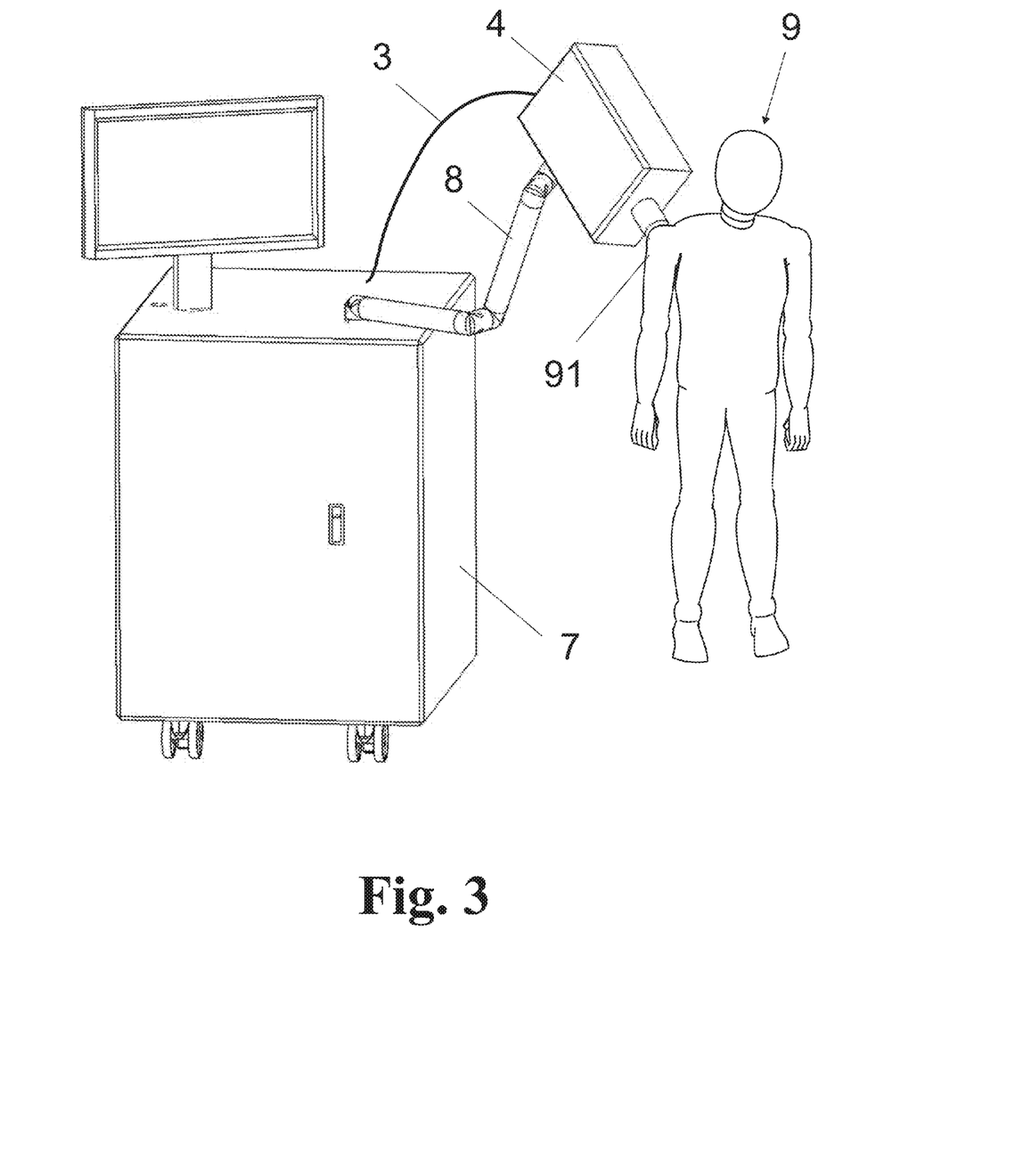
FIG. 3 a three-dimensional illustration of the embodiment of the invention as a mobile, multifunctional laser scanning microscope with measuring head which is freely positionable in space for tomographic examinations on human skin.

As is shown in FIG. 3, the measurement system is a mobile, flexible nonlinear scanning microscope comprising a mobile base device 7 on wheels for freely selectable positioning. A measuring head 4 which is freely movable in space is attached to this base device by a supporting arm 8. Further, two different optical transmission optics 3, an articulated mirror arm 31 and an optical fiber 32, are arranged between the base device 7 and the measuring head 4 for optically guiding the laser radiation needed for the imaging laser scanning. They are provided for transmission of the excitation radiation for different detection methods, for example, and without limiting generality, for multiphoton tomography and CARS tomography, wherein the different excitation beams are superposed collinearly in the measuring head 4. To this end, the system for beam stabilization shown schematically in FIG. 1 with position-sensitive photodetector 5, control unit 6 and controllable tilt mirror 2 is used in the measuring head 4. In this way, it is possible to freely align the measuring head 4 as shown in FIG. 3 on a portion of human skin 91 located anywhere in space as measurement object 9 (person) without resulting in any changes in (deterioration of) the excitation conditions due to the wide range of possibilities for swiveling the measuring head 4.

Various other technical embodiments of the scanning microscope according to the invention, including some of the many possibilities for application, are described in detail in the following examples.

Embodiment Example 2

As was described above referring to FIG. 3, the microscope according to the invention shown in FIG. 4 comprises a mobile base device 7 on wheels for freely selectable positioning.

For multiphoton imaging, there are provided in the base device 7 a short-pulse laser system 71 (5 fs-500 ps; with Gaussian beam profile, e.g., a titanium:sapphire laser) and an optical unit 72 in which the controllable tilt mirror 2 as two-axis tilt mirror 21 couples the laser beam 11 coming from the short-pulse laser system 71 into flexible transmission optics 3 in the form of an articulated mirror arm 31. In this first example, the laser beam 11 is guided to the optical measuring head 4 via the flexible articulated mirror arm 31. A movable supporting arm 8 which comprises a plurality of parts and can be locked in any position allows the optical measuring head 4 to be freely positioned so that the articulated mirror arm 31 is positively driven in a corresponding manner. Therefore, the measuring head 4, including the focusing optics 44 thereof, can be positioned in any orientation to the measurement object 9, in this case in a 90-degree position on a measurement object 9 with perpendicular surface, in the present example, a hanging painting 92 whose composition (material or layer composition) is to be analyzed. In so doing, the target plane 41 is always uniformly illuminated because of the controlling and tracking of the axial direction of the laser beam 11 so that measuring errors resulting from fluctuating excitation radiation are prevented.

The second radiation source required for CARS imaging (in addition to MPT imaging) with a wavelength diverging from the short-pulse laser 71 is generated from a short-pulse laser 71 in that approximately one half of the radiation is coupled out of the laser beam 11 by a beamsplitter 725 and is supplied as laser beam 11' to a frequency conversion unit 73. The laser beam 12 with divergent wavelength emitted from the latter is likewise coupled into the optics unit 72, wherein laser beam 12 is additionally guided via a second tilt mirror 22 controllable in two axes (having the same function as two-axis tilt mirror 21) through a telescope system 722 with variable lens separation and a variable optical delay line 723 and, after passing through an adjustable mirror arrangement 724 and a dichroic mirror 726, is aligned collinearly (spatial superposition of the two beam components along the same axis) with the laser beam 11 of the short-pulse laser 71. After the dichroic mirror 726, both laser beams 11 and 12 are collinearly coupled into the articulated mirror arm 31 and transmitted to the measuring head 4. The conformity of the axes of the two laser beams 11 and 12 is then permanently monitored in the measuring head 4 by checking the center illumination of the position-sensitive photodiode 51 in the test beam 43 which is coupled out of the beam path to the focusing optics 44 via the beamsplitter 42 and correcting the deviation determined for each of the laser beams 11 and 12 via the tilt mirrors 21 and 22 of the optics unit 72 which are controllable in two axes. In this way, it is ensured in any alignment of the articulated mirror arm 31 that the entrance pupil of the focusing optics 44 (target plane 41) is illuminated homogeneously. Instead of the entrance pupil of the focusing optics 44, an aperture-limiting of another optical element used in the measuring head 4 can also be employed.

The overlapping of the individual laser pulses of the two laser beams 11 and 12 with respect to time is realized by manual or motor-actuated adjustment of the variable optical delay line 723. The focus positions of the laser beams 11 and 12 of different wavelengths, which focus positions are separated from one another after the focusing optics 44 by dispersion, can be made to overlap by the telescope system 722 within the measurement object 9 (in the present example of a painting 92).

Within the measuring head 4, the main portion of the laser radiation of the two laser beams 11 and 12 is guided via the beamsplitter 42 into a scanning unit 46 provided for a two-dimensional scan. After the scanning unit 46, the laser radiation is guided via a telescope system 47 into the entrance pupil of the focusing optics 44 and focused by the focusing optics 44 in the painting 92 to be examined.

The scanning unit 46 allows a two-dimensional deflection of the laser beams 11 and 12 inside the focal plane of the focusing optics 44 so that a raster-type two-dimensional scan and excitation of the painting 92 can be carried out.

The tomographic three-dimensional display of the measurement object 9 (as a stack recording over different layers of the painting 92) is made possible by the systematic adjustment of the focusing optics 44 in direction of the optical axis by means of Z-axis positioning means 48.

The signals generated in the focal plane of the focusing optics 44 in the painting 92 by the different excitation beams (laser beams 11 and 12 with different wavelength and pulse rate) are received in an integrating manner by the focusing optics 44 of the measuring head 4 and deflected by two dichroic beamsplitters 451 and 452 for coupling out the measurement signals, for example, autofluorescence signals and SHG signals, separately from the reflected excitation radiation to two measuring detectors, MP detector 54 and CARS detector 55. The evaluation of the MP signals and CARS signals is carried out in the base device 7 in an evaluating unit 61 and can be displayed on a display unit 62 as multidimensional grayscale value distribution.

For image recording based on time correlated single photon counting (TCSPC) with the aim of giving details about atoms, molecules and the environment thereof through measurement of the decay times of the atomic and molecular oscillations, the measuring detectors 54 and 55 can be replaced by detectors of high temporal resolution and their signals can be processed in the evaluating unit 61. For the triggering required in TCSPC measurements, a trigger diode 56 is provided which makes use of a parasitic back reflection of one of the beamsplitters 451 or 452. In this example, the back reflection of beamsplitter 451 is used.

Optionally, a parasitic back reflection of one of the beamsplitters 451 or 452 can also be used for the position-sensitive photodiode 51; with the output signal of the position-sensitive photodiode 51, the control unit 6 controls the stable position of laser beams 11 and 12 with respect to the target plane 41 defined in the measuring head 4 by way of the two-axis tilt mirrors 21 and 22. This position, as alternative to the photodiode 51, is shown in dashes in FIG. 4 and designated as photodiode 51', wherein the parasitic back reflection of beamsplitter 452 is used. This alternative photodiode 51' may be preferable, since it lies closer to the target plane 41 (entrance pupil of focusing optics 44) and so obviates the photodiode 51 arranged in the test beam 43. In this case, beamsplitter 42 can be replaced by a full mirror (not shown).

The directional stability is improved by a factor of 10 to 20 by this laser beam-stabilized excitation of the painting 92 to be measured. An improvement of this kind ensures a homogeneous illumination of the image field in all positions of the measuring head 4 and, therefore, reproducible comparable measurement results.

Embodiment Example 3

Figure 5:
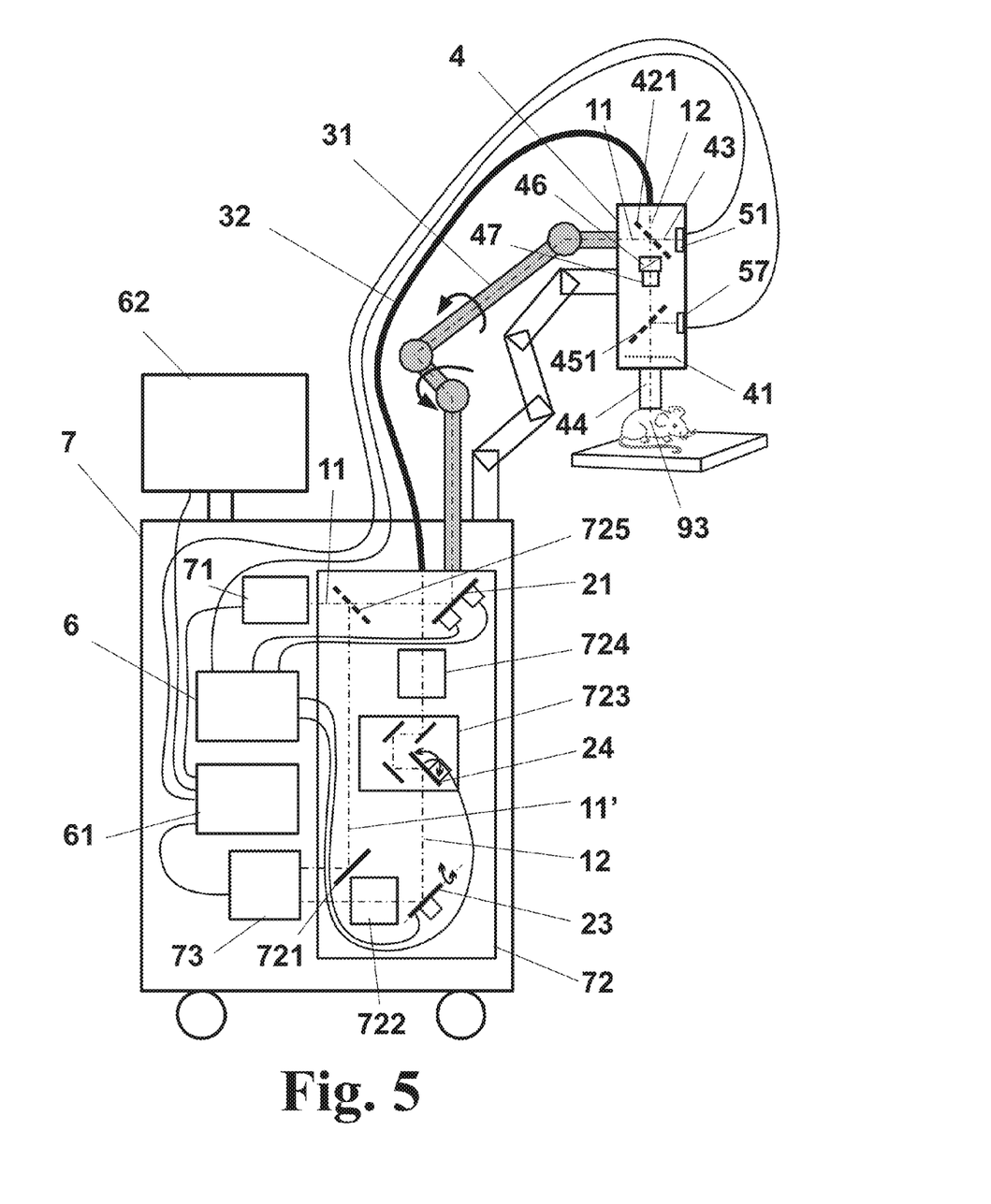
FIG. 5 a schematic illustration of an embodiment of the invention in a flexible laser scanning microscope with two detector systems using an articulated mirror arm and an optical fiber as systems for beam-guiding to the shared measuring head which is aligned in normal position (0°) for examining living tissue of animals, e.g., of a mouse.

FIG. 5 shows the measuring system using an articulated mirror arm 31 and an optical fiber 32 as two separate beam-guiding optical transmission systems 3.

In the same way as in the second example, the short-pulse laser 71 is coupled into the flexible articulated mirror arm 31 by the optical unit 72 via the two-axis tilt mirror 21 and is guided to the optical measuring head 4.

The frequency conversion unit 73 used for generating the additional CARS imaging is provided with the output wavelength generated by the short-pulse laser 71 by means of the laser beam 11' coupled out of the beamsplitter 725 via a deflecting mirror 721 and emits a laser beam 12 with a wavelength deviating from the short-pulse laser 71. In contrast to the previous example, after initially traversing the telescope system 722, the laser beam 12 is then aligned separately in two coordinate directions before the optical delay line 723 by means of a first single-axis tilt mirror 23 and a second single-axis tilt mirror 24 arranged orthogonal thereto. Other than that, it passes through the delay line 723 and the mirror arrangement 724 as was described with reference to FIG. 4. Subsequently, laser beam 12—also diverging from the construction in FIG. 4—does not pass through dichroic beamsplitter 726 for combining with laser beam 11, but rather is coupled separately into a light-conducting fiber 32 and guided via the latter to the measuring head 4.

In the measuring head 4, by means of a suitable dichroic splitter 421 which simultaneously takes on the deflection function for the laser beam 11 and the splitter function for coupling out the test beam 43 to the photodiode 51, the laser beam 12 is collinearly superposed with the laser beam 11 proceeding from the articulated mirror arm 31 and is focused in the tissue of a mouse 93 (as specific measurement object 9).

Further detection and processing of the signals coming back from the tissue of a mouse 93 are carried out, in this example so as to be coupled out via the beamsplitter 451, by means of a shared detector 57 for the generated MP signals and CARS signals. The CARS signals can be discriminated from the MP signals by blocking one of the laser beams 11 or 12 or, alternatively, by changing the phase position (temporal reference) of the two laser beams 11 and 12 relative to one another by means of the delay group 723, so that detector 57 receives only MP signals. Further, by means of in-phase excitation of the two laser beams 11 and 12, the CARS signals and MP signals of the tissue of the mouse 93 can be detected together (in superposition).

Embodiment Example 4

Figure 6:
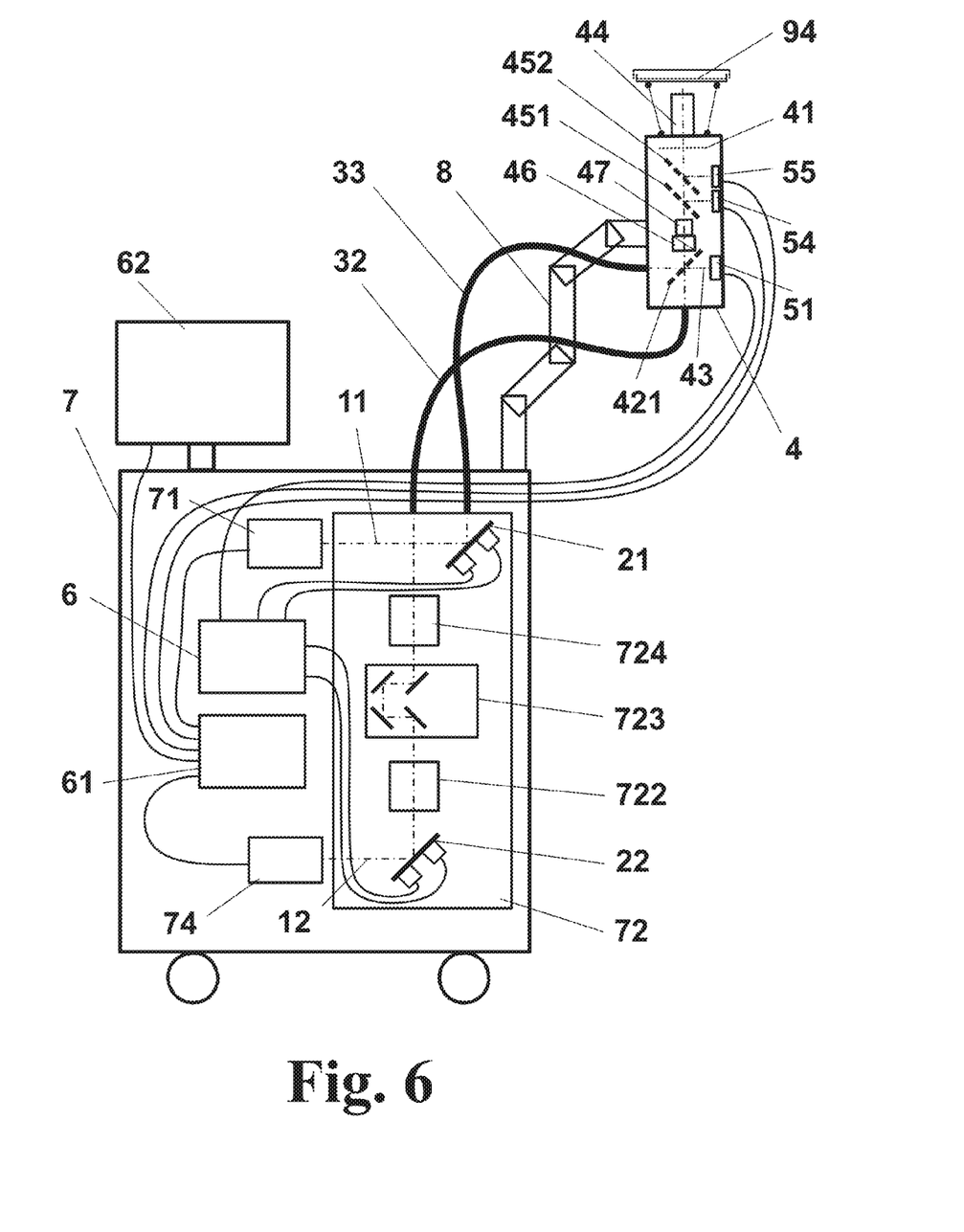
FIG. 6 a schematic diagram of an embodiment of the invention in a tomograph with two detector systems using two optical fibers as system for beam-guiding to the shared measuring head which is aligned as inverted microscope (180-degree position) for examining any substances, e.g., in liquid solution in a Petri dish.

Another advantageous embodiment of the laser scanning microscope is shown in FIG. 6, wherein two optical fibers 32 and 33 are used as beam-guiding optical transmission systems 3.

The two laser beams 11 and 12 with different wavelengths are guided in the optics unit 72 as in the third example, and are aligned and adapted to one another without superposition thereof. In contrast to the previous examples, however, laser beam 12 is generated in a second laser source 74 and, after a somewhat more extensive phase synchronization in the delay group 723 and subsequent mirror arrangement 724, is coupled into the light-conducting fiber 32 (as in the third example referring to FIG. 5). In this case, laser beam 11 is coupled into the second fiber, preferably a monomode fiber 33. Both fibers 32 and 33 are then collinearly superposed in the measuring head 4 similar to the third example by means of a dichroic splitter 421. The stabilized collinear alignment of the laser beams 11 and 12 and the acquisition of the signals excited thereby take place in the same way as described in the second embodiment example.

As measurement object 9, a Petri dish 94 filled with liquid or solid substances can be rigidly fixed to the measuring head 4 (in the simplest case, e.g., with double-sided adhesive tape) or can be movably coupled to a positioning stage (e.g., two-axis or three-axis mechanical stage, not shown). This allows a microscopic imaging using very few technical resources. Instead of a Petri dish 94, substances can also be examined in the same way in microtiter plates. The inverted microscope arrangement shown schematically in FIG. 6 accordingly makes it possible to examine any specimens such as, e.g., samples embedded in nutrient solutions, powdered or granulated solids materials or also solid bodies (near-surface areas).

The advantages of the described MPT system with CARS detection over conventional non-flexible systems consist in the low-weight measuring head 4 which is freely positionable in space by means of the optical articulated arm 31 and/or light-conducting fibers 32, 33 and in the mobile base device 7. An arrangement of this kind allows the operator to rapidly carry out combined high-resolution measurements (economizing on time and cost) in a reproducible manner and in so doing to have a microscope measuring arrangement which can carry out a large number of measurements in different parts of the measurement object 9 (particularly on the human body or animal body) for object surfaces in any orientation in a completely equivalent (compatible) manner and without moving the measurement object (e.g., repositioning of patients) or taking samples from the measurement object 9.

Further, the flexible positioning of the measuring head 4 enables so-called inverse imaging as is popularly used in conventional microscopy.

In contrast to conventional microscope systems which are available only as upright microscopes (0°) or inverted microscopes (180°), the present invention having the measuring head 4 with unlimited movability also allows arrangements in 90-degree positions or any position diverging therefrom. Accordingly, it also allows measurements on standing objects, e.g., examinations of mold cultures on walls, plant parts in a planted area, material analysis (see FIG. 4), animal examinations (see FIG. 5) and skin examinations on humans (FIG. 3) as well as a wide range of forensic examinations and can also be used as an inverted laser scanning microscope for examining any liquid or solid substances (FIG. 6).

Further, with a suitably adapted attachment (not shown) at the measuring head 4, it is possible to use a positioning table (mechanical stage) at the measuring head 4 to offer conventional microscope performance permitting high-resolution examinations of macroscopic sample areas at any location as a result of the mobility of the scanning microscope (base device 7).

The coupling of diagnostic imaging systems of multiphoton fluorescence microscopy, multiphoton SHG microscopy and/or CARS microscopy has the advantage over separate diagnostic systems that methods of multiphoton excitation and imaging, multiphoton SHG excitation and imaging and CARS excitation and imaging are combined in a compact mobile base device 7 with flexible measuring head 4. The proposed arrangement with flexible articulated arm 31 or optical fibers 32, 33 enables a free positioning of a measuring head 4 without limiting resolution and without faulty signals resulting from a misalignment of the excitation radiation due to the fact that the excitation radiation is reliably detected and corrected in a simple and robust manner, and imaging and evaluation are accordingly guaranteed with minimal errors.

LIST OF REFERENCE NUMERALS

1 laser
11 laser beam (excitation beam)
12 laser beam (second excitation beam)
13 beam profile
2 (controllable) tilt mirror
21, 22 two-axis tilt mirror
23, 24 single-axis tilt mirror
3 transmission optics
31 articulated mirror optics
32 light-conducting fiber 33 monomode fiber
4 measuring head
41 target position
42 beamsplitter
421 dichroic splitter
43 test beam
44 focusing optics
45 signal out-coupling splitter
451 dichroic beamsplitter
452 dichroic beamsplitter
46 scanning unit
47 telescope system
48 Z-axis positioning
5 (position-sensitive) photodetector
51 (circular) photodiode
52, 53 signal components (in X and Y direction)
521, 531 maximum
54 (MP) detector
55 (CARS) detector
56 trigger diode
57 shared detector
6 control unit
61 evaluating unit
62 display unit
7 (mobile) base device
71 short-pulse laser
72 optics unit
721 deflecting mirror
722 telescopic system
723 delay group
724 mirror arrangement
725 beamsplitter
726 dichroic mirror
73 frequency conversion unit
74 second laser source
8 supporting arm
9 measurement object
91 human skin
92 painting
93 mouse tissue
94 Petri dish (with liquid substance)

What is claimed is:

1. A flexible nonlinear laser scanning microscope for non-invasive three-dimensional detection comprising:
   at least one radiation source which generates an excitation beam of pulsed laser radiation for initiating a secondary radiation;
   a measuring head having at least one detector system and focusing optics for focusing the excitation beam in a measurement object, collecting secondary radiation emitted from the object, and directing the secondary radiation to the at least one detector system;
   flexible transmission optics for transmitting the excitation beam from the at least one radiation source to the measuring head and enabling the measuring head to be freely pivotable and rotatable in space and flexibly positionable for carrying out upright microscopy, inverted microscopy, and microscopy at any solid angle;
   at least one controllable tilt mirror receiving the excitation beam from the at least one radiation source, and deflecting and aligning the excitation beam through the flexible transmission optics to the measuring head to keep the excitation beam arranged concentrically to an aperture-limited optical element of the focusing optics of the measuring head in response to movement of the measuring head;
   a beamsplitter for coupling a test beam split from the excitation beam, the beamsplitter being disposed in the measuring head in front of the focusing optics;
   a spatially resolving photodetector for determining a beam position of the excitation beam, the photodetector being disposed in a position to receive the test beam from the beamsplitter conjugate to a target position of the excitation beam in relation to the aperture-limited optical element of the measuring head, wherein a center alignment position of the test beam on the photodetector corresponds to a normal orientation and stabilization of the excitation beam in the target position; and
   a control unit for driving the at least one controllable tilt minor, in response to receiving the test beam from the spatially resolving photodetector, by determining a deviation of the test beam from the center alignment position and adjusting the at least one controllable tilt minor to direct the test beam to the center alignment position to achieve stabilization of the excitation beam in the target position.

2. The laser scanning microscope according to claim 1, wherein the at least one controllable tilt mirror is driven by a mirror holder by capacitive, inductive or piezo actuators, stepping motors or DC motors.

3. The laser scanning microscope according to claim 1, wherein the at least one controllable tilt mirror is comprised of a two-axis mirror holder or of two single-axis minor holders.

4. The laser scanning microscope according to claim 1, wherein an entrance pupil of the focusing optics or of another aperture-limited optical element is selected as the target position of the excitation beam.

5. The laser scanning microscope according to claim 1, wherein the beamsplitter for generating the test beam is comprised of either a reflection beamsplitter or a transmission beamsplitter for guiding the excitation beam in the measuring head.

6. The laser scanning microscope according to claim 1, wherein the beamsplitter for coupling out the test beam is a dichroic mirror for collinear in-coupling of two different excitation beams.

7. The laser scanning microscope according to claim 1, wherein the photodetector is a circular photodiode.

8. The laser scanning microscope according to claim 1, wherein the photodetector further controls stability of the excitation beam by the control unit through the transmission optics and provides signals for determining and controlling a pointing stability of the excitation laser.

9. The laser scanning microscope according to claim 1, wherein the detector system for the secondary radiation comprises a detector for MPT (MultiPhoton Tomography) imaging or SHG (Second Harmonic Generation) imaging, and wherein a flexible optical articulated arm permits free positioning of the measuring head in space to ensure reproducible MPT imaging.

10. The laser scanning microscope according to claim 1, wherein the at least one detector system for the secondary radiation comprises detectors for MPT imaging and for CARS (Coherent Anti-Stokes Raman Scattering) imaging, and wherein a shared flexible optical articulated arm permits free positioning of the measuring head in space and generates simultaneous co-located imaging from MPT signals and CARS signals.

11. The laser scanning microscope according to claim 1, wherein the detector system for the secondary radiation is designed for MPT imaging and for CARS imaging, and wherein a flexible optical articulated arm and a separate optical fiber permit free positioning of the measuring head in space and generate a simultaneous co-located imaging from MPT signals and CARS signals.

12. The laser scanning microscope according to claim 1, wherein the detector system for the secondary radiation is designed for MPT imaging and for CARS imaging, and wherein two separate optical fibers permit free positioning of the measuring head in space and generates simultaneous co-located imaging from MPT signals and CARS signals.

13. The laser scanning microscope according to claim 1, wherein the detector system for the secondary radiation comprises a shared measuring detector for MPT imaging and for CARS imaging, and wherein means for periodically interrupting the CARS excitation allow a separation of MPT imaging with respect to a combined signal display.

14. The laser scanning microscope according to claim 1, wherein the at least one detector system for the secondary radiation comprises TCSPC detectors for MPT imaging and a trigger diode using a back reflection of another beamsplitter for coupling out measurement signals.

15. The laser scanning microscope according to claim 1, wherein the measuring head is mechanically supported by a flexible supporting arm which can be locked in any position at a mobile base device, the flexible supporting arm positively driving the transmission optics, the mobile base device comprising:
  the at least one radiation source for generating the excitation beam of pulsed laser radiation;
  an optics unit for synchronizing the pulsed laser radiation and aligning the transmission optics to the measuring head;
  the control unit for stabilizing a direction of the excitation beam in the measuring head; and
  an evaluating unit for processing signals transmitted from the at least one detector system of the measuring head for imaging by a display unit.

16. A flexible nonlinear laser scanning microscope for noninvasive three-dimensional detection comprising:
  at least one radiation source which generates an excitation beam of pulsed laser radiation for initiating a secondary radiation;
  a measuring head having at least one detector system and focusing optics for focusing the excitation beam in a measurement object, collecting the secondary radiation emitted from the object, and directing the secondary radiation to the at least one detector system;
  flexible transmission optics for transmitting the excitation beam from the at least one radiation source to the measuring head and enabling the measuring head to be freely pivotable and rotatable in space and flexibly positionable for carrying out upright microscopy, inverted microscopy, and microscopy at any solid angle;
  at least one controllable tilt mirror for deflecting and aligning at least one excitation beam of the at least one radiation source, the controllable tilt mirror serving to align the at least one excitation beam in the measuring head through the transmission optics in order to keep the excitation beam arranged concentrically to an aperture-limited optical element of the focusing optics of the measuring head in any position of the measuring head;
  a beamsplitter for coupling a test beam split from the excitation beam, the beamsplitter being disposed in the measuring head in front of the focusing optics;
  a spatially resolving photodetector for determining a beam position of the excitation beam, the photodetector being disposed in a position of the test beam conjugate to a target position of the excitation beam in relation to the aperture-limited optical element of the measuring head, wherein a center alignment of the test beam on the photodetector corresponds to a normal orientation of the excitation beam in the target position; and
  a control unit for driving the at least one controllable tilt minor depending on a determined deviation of the test beam from its center alignment on the photodetector to achieve a stabilization of the excitation beam in the target position irrespective of a magnitude of a position-dependent impairment of the transmission optics,
  wherein the at least one detector system comprises TCSPC detectors for MPT imaging, and a trigger diode using a back reflection of another beamsplitter for coupling out measurement signals.

* * * * *